United States Patent [19]

Richey et al.

[11] Patent Number: 4,547,892

[45] Date of Patent: Oct. 15, 1985

[54] CARDIAC IMAGING WITH CT SCANNER

[75] Inventors: Joseph B. Richey, Shaker Heights; Robert H. Wake, Warrensville Heights; Ronald G. Walters, Aurora; Willard F. Hunt, Cleveland; Steven L. Cool, Shaker Heights, all of Ohio

[73] Assignee: Technicare Corporation, Solon, Ohio

[21] Appl. No.: 106,730

[22] Filed: Dec. 26, 1979

Related U.S. Application Data

[63] Continuation of Ser. No. 783,717, Apr. 1, 1977, abandoned.

[51] Int. Cl.$^4$ .......................... A61B 5/02; A61B 6/00; H05G 1/44
[52] U.S. Cl. ........................................ 378/8; 128/653; 128/661; 378/95
[58] Field of Search ................... 378/4, 8, 14, 95, 148, 378/145, 150, 146, 10, 11; 128/660, 661, 653

[56] References Cited

U.S. PATENT DOCUMENTS

| | | | |
|---|---|---|---|
| 3,924,131 | 12/1975 | Hounsfield | 378/11 |
| 3,952,201 | 4/1976 | Hounsfield | 378/8 |
| 3,954,098 | 5/1976 | Dick et al. | 128/660 |
| 3,993,995 | 11/1976 | Kaplan et al. | 378/95 |
| 4,031,395 | 6/1977 | Le May | 378/14 |
| 4,037,585 | 7/1977 | Gildenberg | 378/8 |
| 4,126,785 | 11/1978 | Hounsfield | 378/8 |
| 4,143,273 | 3/1979 | Richey et al. | 378/150 |
| 4,150,293 | 4/1979 | Franke | 378/146 |

Primary Examiner—Alfred E. Smith
Assistant Examiner—T. N. Grigsby
Attorney, Agent, or Firm—Audley A. Ciamporcero, Jr.; Michael A. Kaufman

[57] ABSTRACT

The patient's ECG signal is employed in a traverse-and-rotate type CT scanner as a time base for triggering the beginning of a traverse such that the traveling beam reaches the heart at a desired phase of the cardiac cycle. For a purely-rotational-type CT scanner, continuously generated scan data is only stored for corresponding phases of successive cardiac cycles. Alternatively, gating of the beams themselves can be controlled by the ECG signal. The use of a pacemaker to stabilize the cardiac period is described along with a system for recognizing unacceptable variations in the cardiac period. In a traverse-and-rotate-type fan-beam CT scanner, the effective beam width is narrowed to hasten the traverse of the heart.

13 Claims, 8 Drawing Figures

CARDIAC IMAGING WITH CT SCANNER

BACKGROUND OF THE INVENTION

This application is a continuation of application Ser. No. 783,717, filed Apr. 1, 1977, now abandoned.

Computerized tomographic X-ray or gamma ray scanners (CT scanners) reconstruct an image representing a single tomogram of the radiation absorptivity of tissues from data collected from numerous coplanar scan lines. The widest application of CT scanners thus far has been for brain studies. Being stationary when supported in the CT scan circle, all parts of the brain generally remain in the same location during each of the numerous scans required for constructing a single tomographic image. However, involuntary muscular activity makes accurate image reconstruction of other parts of the body difficult. This problem is presented with both basic types of CT scanners, namely, traverse-and-rotate type CT scanners and purely-rotational-type CT scanners.

Heart structures, for example, are in constant motion. While the heart period is on the order of one second, distinct physiological phases of the cardiac cycle, for example, the periods referred to as end systole (ES) and end diastole (ED) last on the order of 1/20 and 1/5 of a second, respectively. That is, if all of the scan lines needed to reconstruct an image of the heart could be produced in less than 1/20 of a second, the motion of the heart would be effectively frozen during either of these periods. This speed, however, is difficult for conventional CT scanners which normally require from about 5 seconds to several minutes to collect the scan data for a single image.

The objectives of cardiac imaging in general are visualizing the sizes of the cardiac chambers, estimating contractilities of the chambers, comparing chamber wall motions, locating aneurysm and areas of myocardial infarction and detecting mitral stenosis. Most of these objectives are, of course, difficult to attain using conventional exposed film X-ray techniques because the differences in absorption or density of heart tissues and blood is not sufficient to confidently distinguish these features at safe radiation dosages and because a tomogram or cross-sectional slice image is not generated.

An electrocardiogram (ECG) is produced by recording the amplitude of electrical activity associated with the heart muscle versus time. In ultrasound imaging, the ECG signal has been used before as a synchronizing device for producing a stop-action image of the heart. See, for example, U.S. Pat. No. 3,954,098. Some ultrasound imaging systems have used computerized sorting and assembling multiple images per nominal heart cycle with recorded data from several heart cycles.

Ultrasound imaging differs fundamentally from X-ray imaging. X-rays are not normally reflected detectably by tissue; that portion which is not absorbed is merely transmitted. All conventional X-ray imaging machines operate in the transmission mode. While ultrasound imaging can be carried out in the transmission mode in some instances, conventional ultrasound cardiac imaging, particularly ECG-gated imaging, is only done in the reflecting or echo mode. Ultrasound imaging involves pinpointing each partially reflecting surface for a given pulse of sound energy by measuring the round trip transit time for reception of the echoes, just as in sonar. A single pulse of radiation, however, in the X-ray transmission mode results in a single datum describing the total absorption encountered over the entire path of the X-ray beam; that is, the location of structures is not identifiable from one pulse.

SUMMARY OF THE INVENTION

The general purpose of the invention is to produce an image of the radiation attenuation of the heart at a desired phase of the cardiac cycle. The patient's ECG signal is employed in a traverse-and-rotate-type CT scanner as a time base for triggering the beginning of a traverse such that the traveling beam reaches the heart at a desired phase of the cardiac cycle. For a purely-rotational-type CT scanner, continuously generated scan data is only stored for corresponding phases of successive cardiac cycles. Alternatively, gating of the beams themselves by shuttering or switching the power supply can be controlled by the ECG signal. The use of a pacemaker to stabilize the cardiac period is described along with a system for recognizing unacceptable variations in the cardiac period and discarding corresponding scan data. In a traverse-and-rotate-type fan-beam CT scanner, the effective beam width is narrowed to reduce the duration of the traverse of the heart.

DESCRIPTION OF THE PREFERRED EMBODIMENTS

Figure 1:
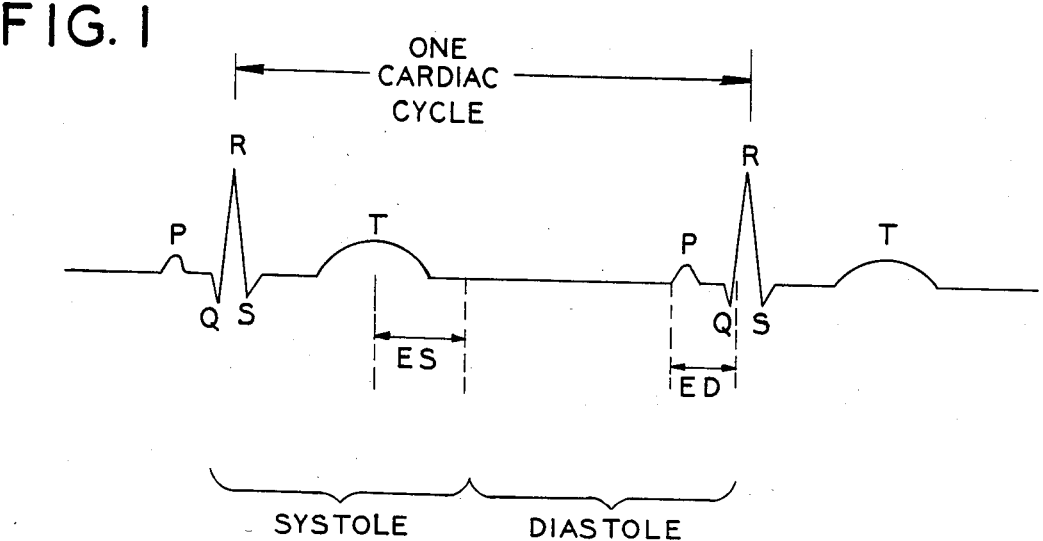
FIG. 1 is an ECG waveform.

The ECG waveform shown in FIG. 1 presents features designated by the letters P, Q, R, S and T. The group of features Q, R and S is referred to as the QRS complex, in which the R-feature or R-wave is the most prominent, highest amplitude feature of the entire ECG. Moreover, the narrow pulse width of the QRS complex and in particular the R-wave, provides a digital clock pulse for timing the cardiac cycle.

The cardiac cycle is usually defined as beginning with the R-wave and continuing until the occurrence of the next R-wave. Heart functions are characterized by two distinct periods called systole and diastole. In systole, the heart muscle is contracting the volume of the left ventricle to pump the contents out through the aortic valve. During diastole, the left ventricle is filling through the mitral valve. At the end of systole (ES), the left ventricle has its smallest volume since it has contracted to pump blood out. The end of diastole (ED) is the point at which the left ventricle has its largest volume since it is filled with blood ready to be pumped out. These two extremes of heart function, end of systole and end of diastole, are of interest, for example, in determining fractional ejection, i.e., the ratio of minimum-to-maximum ventricular volume. Each of these features, end of systole and end of diastole, lasts for an interval on the order of 1/10 second and occurs once every cardiac cycle.

Figure 2:
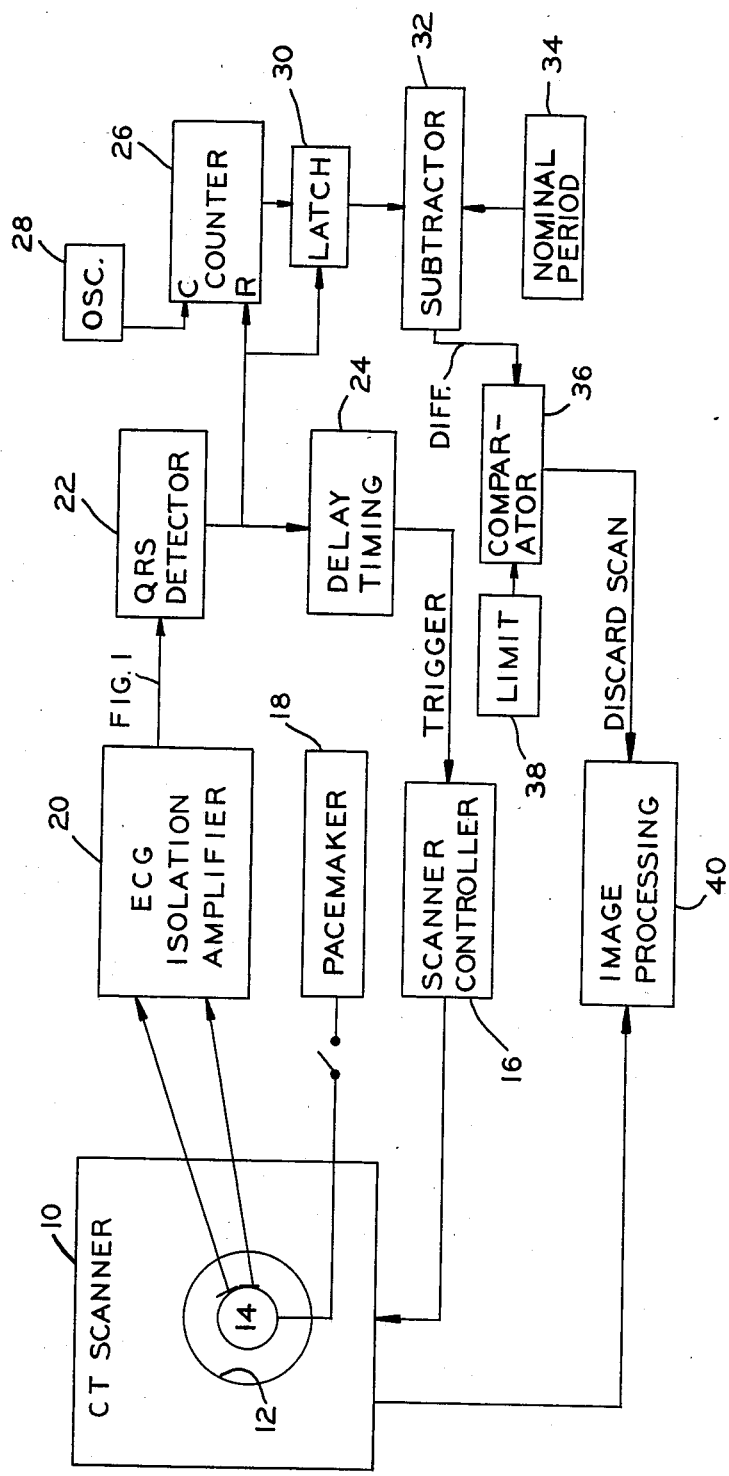
FIG. 2 is a block diagram illustrating an ECG-controlled CT scanner system according to the invention.

FIG. 2 shows a conventional traverse-and-rotate-type CT scanner having a scan circle 12 defining a scan plane in which the patient 14 is positioned such that the scan plane preferably intersects the left ventricle, left atrium or aortic root of the heart. The mechanical operation of the traverse-and-rotate mechanism and the beam shutter is controlled by a scanner controller 16. An external pacemaker 18 may be employed to stabilize the cardiac period of a patient with irregular heart rate. The ECG signal from the patient is applied by an isolation amplifier 20 to a QRS complex detector 22 whose output is a digital timing pulse corresponding to each R-wave of the patient's live ECG signal. The items 20 and 22 are commercially available units, for example, Hewlett Packard Corporation, Model Nos. 7807C and 7830A. The output of the QRS detector 22 is fed to a delay timing circuit 24 which provides a trigger pulse to the CT scanner controller 16.

Figure 3:
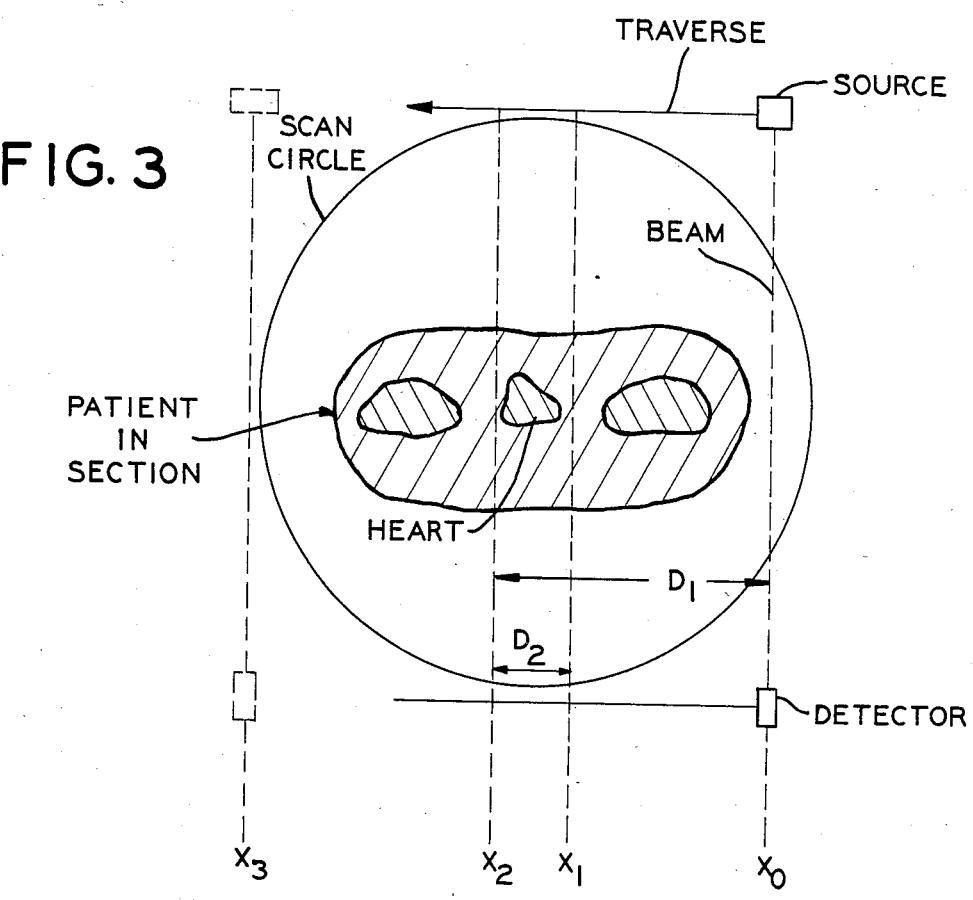
FIG. 3 is a schematic diagram indicating the CT scanner beam's traverse in relation to the patient's heart.

If the objective is to acquire an image of the heart at the end of diastole with the left ventricle fully expanded, the trigger pulse is timed to be applied to the scanner controller 16 sufficiently in advance of the end of diastole so that the scanner controller 16 can begin the traverse of the radiation beam, as shown in FIG. 3, from point $x_0$ so that by the time the beam travels distance $D_1$ to position $x_1$ where it first begins to intersect the heart, the heart will be in the end of diastole stage. Of course, the beam must be traversing at a rate sufficient to traverse the width of the heart in this presentation in approximately less than 1/10 of a second. Thus, the distance $D_2$ from point $x_1$ to the point $x_2$ would determine the minimally acceptable speed of traverse. The consequence of traveling too slowly through the distance $D_2$ in FIG. 3 would be a blurring of some of the moving heart structures.

The delay time provided by the circuit 24 in FIG. 2 is determined by three parameters: (1) the speed of the traverse of the beam; (2) the position of the heart in the scan circle 12; and (3) a predication of when the particular phase of interest, for example end of diastole, will occur in the average or nominal cardiac cycle of the patient. The speed of traverse of the beam is normally a known constant value. However, the speed can be monitored during the scan to compensate in successive scans for any variations in the average scan speed. The position of the heart can be determined in two ways: the heart's position can be considered by adjusting the patient's position in the scan circle or the patient can be prescanned and the location of the heart determined by the scanner operator from the reconstructed image. Prediction of the time that the heart will be in a particular phase, such as end diastole, requires a knowledge of the heart rate, as measured by the interval between R-waves, and the average time elapsed from an R-wave up to the phase of interest. This information is derived from the patient's electrocardiogram. It could also be derived from a phonocardiogram or pressure measurements. The ultimate objective is to synchronize the CT cardiac scanning with cardiac contractility. Use of the ECG signal is a means for inferring the phases of the cardiac contractility curve. Contractility measurement devices may be employed to determine the contractile state of the heart directly and more accurately.

These parameters are taken into consideration in setting the delay implemented by the timing circuit 24. After the R-wave signal from the QRS detector 22, the delay timing circuit 24 pauses before issuing a trigger pulse for an interval of time which can be represented as follows:

$$\text{Time Interval} = T_{ED} - D_1/R_{avg}$$

where $T_{ED}$ is the predicted time from a given R-wave to the beginning of the end of the diastole phase; $D_1$ is the position of the heart in terms of the distance the beam covers from the starting point $x_0$ until reaching the center wall of the heart (or some other point of interest); $R_{avg}$ is the average speed of the traversing beam; and $D_1/R_{avg}$ is the predicted elapsed time from the beginning of the traverse to the point where the center beam intersects the center of the heart.

For any patient the period of the cardiac cycle, as shown in FIG. 1, from one R-wave to the next R-wave always varies to some degree. The timing of the triggering of a traverse is based solely on the occurrence of the last R-wave and the predicted time for beginning of the end of diastole or end of systole whichever phase is being imaged. It is entirely possible that the prediction may not be borne out. If the cardiac cycle, which the scanner is preparing to sample, is one of sufficiently increased or reduced period, the end of diastole or end of systole will occur at a significantly different time. Thus, it is advisable to place tolerance limits on the cardiac period in order to distinguish acceptable and unacceptable scan data.

The system of FIG. 2 merely illustrates one form of digital circuitry for performing heart period dissemination. In practice, it may be preferable to implement these functions with software using the CT scanner computer associated with image processing the machine control. The output of the QRS detector 22 is passed to the reset input of a digital counter 26 clocked, for example, at one hundred or one thousand Hertz by a stable frequency oscillator 28. The parallel binary output of the counter 26 is passed via a latch circuit 30 to a subtractor circuit 32. The latch 30 operates as a digital sample-and-hold circuit which holds the count attained by the counter 26 immediately before being reset by the next R-wave. The number contained in latch 30 is compared by the subtractor 32 to the number held in storage 34 representing the nominal period of the patient's cardiac cycle. The difference between the counts for the actual and nominal periods is passed to a comparator 36. A reference number indicating a tolerance limit on the difference between the actual and nominal periods is provided by the limit circuit 38. If the difference exceeds the limit provided by the circuit 38, the binary comparator output alerts the image processing unit 40 associated with the CT scanner 10 to discard the scan data corresponding to the irregular period.

The actual tolerance limits on cardiac period depend on the phase being imaged. For example, the tolerance for imaging end of diastole will be smaller than the tolerance for end of systole since the interval to end of diastole is generally regarded as proportional to the cardiac period and comes at the very end of the cardiac cycle. Thus, in addition to setting the delay timing in accordance with the phase of interest, the tolerance limits for an acceptable cardiac period should also be adjusted accordingly.

Figure 4:
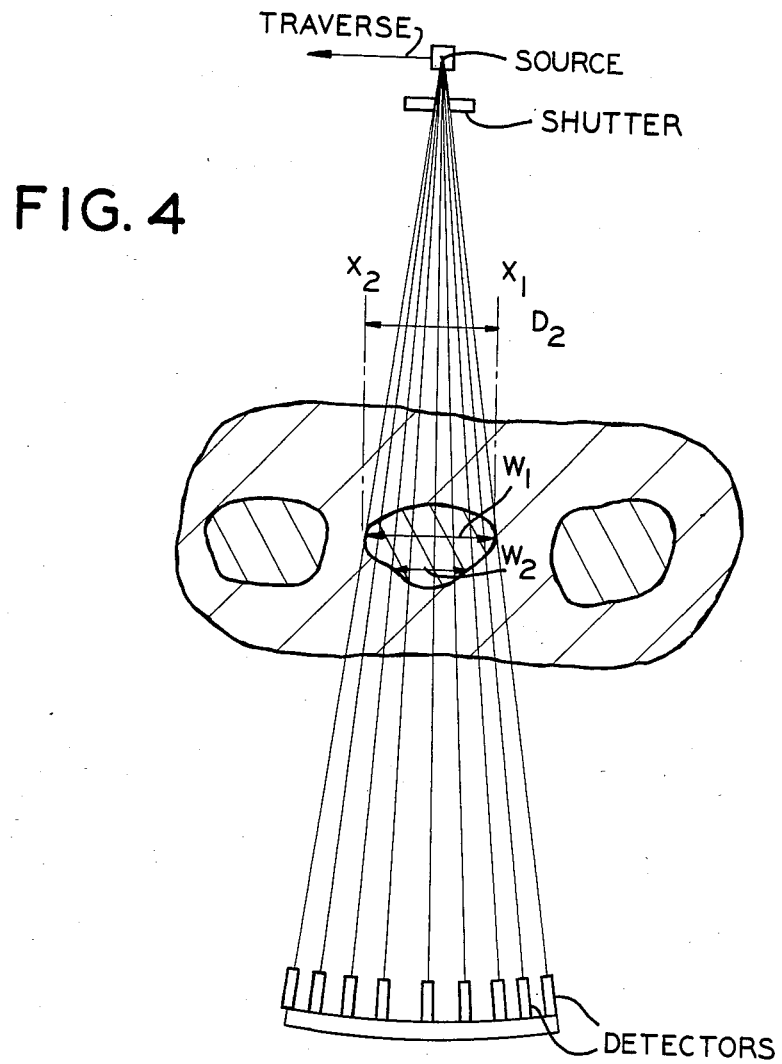
FIG. 4 is a schematic diagram of a traverse-and-rotate-type fan-beam CT scanner illustrating the beam pattern intersecting the patient's heart.

Instead of employing a single beam as shown schematically in FIG. 3, several CT scanning devices currently on the market, such as the Delta-Scan model marketed by Ohio-Nuclear, Inc., traverse with a fan-shaped pattern of beams as shown in FIG. 4. The fan-beam pattern covers a width $W_1$ where it intersects the heart. The consequence of the width of the beam pattern is that it takes longer for the entire plurality of beams to traverse the heart from point $x_1$ to point $x_2$. As is the case in FIG. 4, if the width of the beam is approximately equal to $D_2$, i.e. the width of the heart in the plane in the scan direction, the time relative to a narrow beam scan will be doubled for a full heart traverse of all of the beams in the fan pattern. To alleviate this problem, the effective beam width can be narrowed, for example to $W_2$, by ignoring or "throwing out" data from several of the peripheral detectors. For example, the data from the two outermost detectors on either side can be ignored. Alternatively, a shutter can be employed as shown in FIG. 4 to block certain peripheral rays thus narrowing the actual pattern. The effect of either of these remedies is to narrow the fan-beam width at the heart so that the distance $D_2$ can be traversed more quickly. The faster the interval $D_2$ is traversed, the less motion will be present to cause blurring in the image. Thus, the precision of the stop-action effect can be increased by omitting data from peripheral beams to achieve a shorter effective time window. Blocking the beams instead of ignoring the data from the detectors has the advantage of eliminating unnecessary X-ray dosage. However, removing several of the beams will cause a slight increase in the overall scan time for completing the image.

Figure 5:
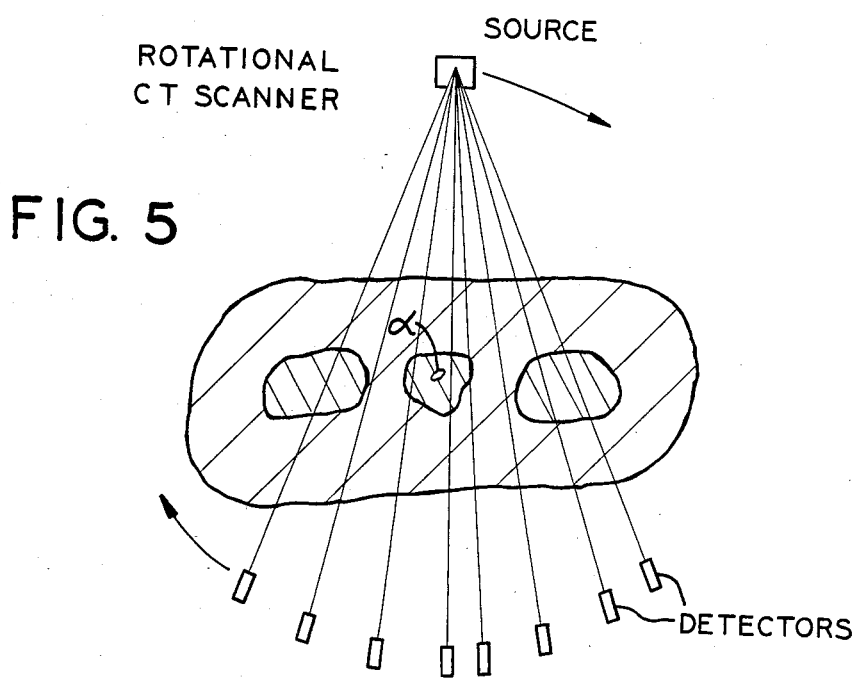
FIG. 5 is a schematic representation of the beam pattern of a purely-rotational-type CT scanner.
Figure 6:
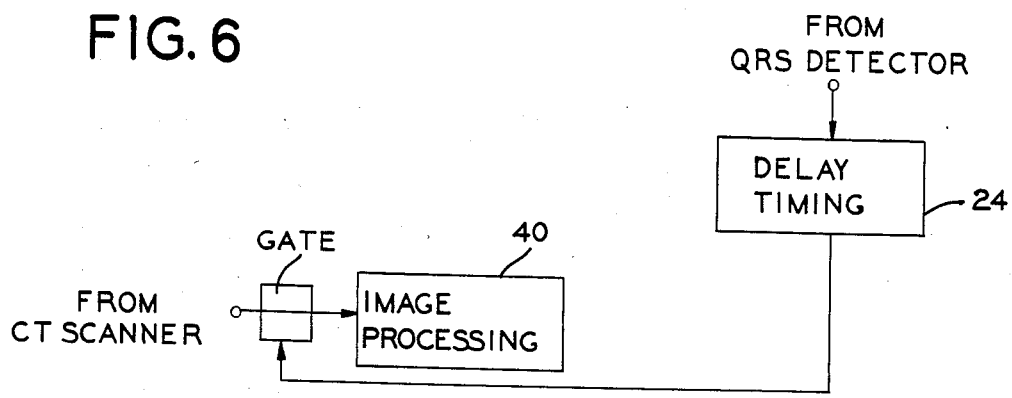
FIGS. 6, 7 and 8 are detail block diagrams illustrating different systems of ECG-gating for a purely-rotational-type CT scanner.

Cardiac imaging can also be accomplished with a purely rotational CT scanner as shown in FIG. 5 wherein $\alpha$ is the rotational axis. In this case, however, since rotation of the source and detectors is continuous, instead of triggering the mechanical traverse at the right point so that data is acquired in the phase of interest, scan data is generated continuously. The patient's ECG signal can be used as in FIG. 6 to gate the storage of data by the image processing unit 40. The delay timing circuit is thus used to open a time window during the appropriate phase in each cardiac cycle in which data is collected. Several phases can be gated with the ECG signal or even a full set of images covering every distinct physiological point in the cardiac cycle can be generated. These images can be sequenced then to produce a movie or cine presentation of the subject's heart. This alternate also includes the possibility of a semi-circle of stationary detectors and a rotating source or stationary source(s) and rotating detectors.

Figure 7:
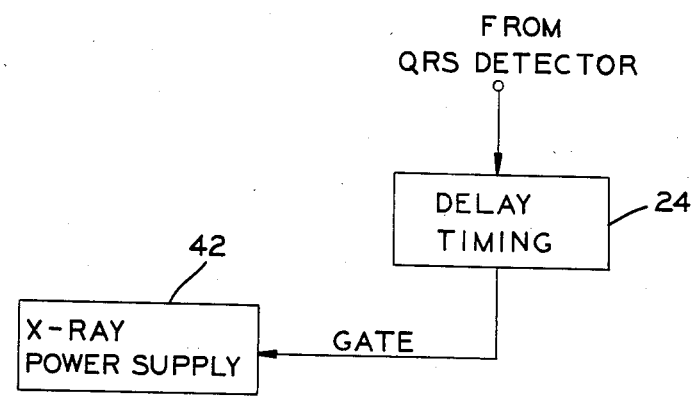
Figure 8:
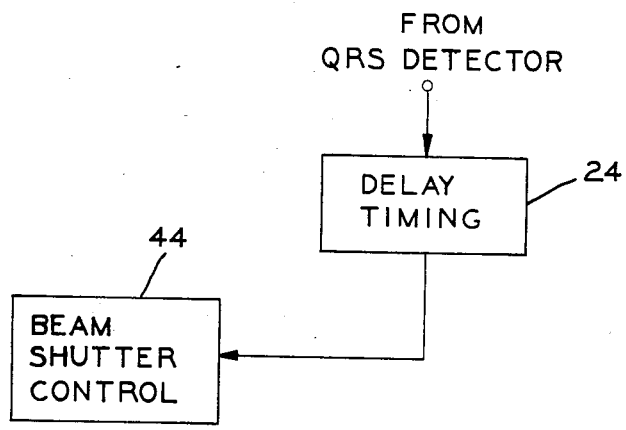

In order to minimize X-ray dosage to the patient, the X-ray tube could be gated on and off as indicated by the gating of X-ray power supply 42 in FIG. 7, or dynamically shuttered as indicated in FIG. 8 by the gating of beam shutter control 44, which would open the shutter blocking the beams only during the physiological phase of interest during each cardiac cycle.

In addition to cardiac gating, chest motion from breathing can be removed from the image by using pulmonary gating. Scan data would only be stored at times when the phase of the cardiac cycle under investigation coincided with a particular phase of the pulmonary cycle.

The above-described embodiments are intended to be illustrative, not restrictive. For example, the use of the interval end of diastole or end of systole is intended to be illustrative of the use of any interval of interest. Moreover, the same techniques disclosed herein may be applicable to other physiological functions besides the heart. The invention is applicable, of course, to any type of beam transmission subject to differential tissue absorption such as X-rays, $\gamma$ rays, etc. The scope of the invention, however, is defined by the appended claims and all variations which fall within the range of equivalents thereto are intended to be embraced therein.

We claim:

1. A radiographic apparatus for imaging a planar slice of a patient's heart, the apparatus comprising:

a CT scanner comprising a source of at least one beam of radiation, scan means for scanning the beam of radiation relative to the heart substantially in the plane of the slice, data generating means for generating image data from detected radiation which has crossed through the scan circle, means for processing image data from the data generating means to reconstruct a tomographic image of the planar slice;

cardiac cycle monitoring means for producing a repeating pulse signal indicative of the same functional point in each successive cardiac cycle of the patient;

control means responsive to said pulse signal for causing said processing means to process image data generated during the same selectable phase in successive cardiac cycles, said control means including selectable delay means for delaying said pulse signal for a selectable duration thereby selecting said selectable phase in the cardiac cycle; and, irregular cardiac cycle sensing means comprising discriminator means responsive to said pulse signal for producing an output signal to command said processing means to discard image data when the corresponding cardiac period varies from the patient's nominal cardiac period beyond predetermined limits, whereby data from irregular cardiac cycles is prevented from degrading the tomographic image.

2. The apparatus as set forth in claim 1 wherein said CT scanner comprises a traverse-and-rotate-type CT scanner system, wherein said scan means comprises means for laterally traversing the beam of radiation and means for rotating the beam of radiation, and wherein said control means further comprises means responsive to said pulse signal for generating a trigger pulse to initiate a lateral traverse such that the traveling beam will reach the heart substantially coincidental with said selected phase in the cardiac cycle.

3. The apparatus as set forth in claim 2 wherein said source of radiation generates a plurality of coplanar beams of radiation in a fan-shaped pattern, and wherein said traverse-and-rotate-type CT scanner further comprises means for omitting image data associated with at least one peripheral beam in said fan-shaped pattern in order to narrow the effective width of said pattern of beams.

4. The apparatus as set forth in claim 3, wherein said omitting means includes means for blocking at least one of said peripheral beams.

5. The apparatus as set forth in claim 1 wherein said discriminating means further comprises means for adjusting said limits according to the selected phase in the cardiac cycle.

6. The apparatus as set forth in claim 1, further comprising external pacemaker means for stabilizing the patient's cardiac period.

7. The apparatus as set forth in claim 1, further comprising means for producing a pulmonary pulse signal indicative of the same functional point in each successive pulmonary cycle of the patient, said control means further being responsive to said pulmonary pulse signal for causing said processing means to process image data in a selected phase in corresponding cardiac cycles coinciding with a particular phase of the pulmonary cycle in order to eliminate errors from chest motion due to breathing.

8. The apparatus as set forth in claim 1, wherein said CT scanner is a purely-rotational-type CT scanner wherein said scan means rotates the beam of radiation relative to the heart, and wherein said control means further including:

means responsive to said pulse signal for generating a gate signal having timing and duration corresponding to the predicted occurrences of said selected phase cycle; and means responsive to said gate signal for enabling the processing means to process image data generated during said gate signal.

9. The apparatus as set forth in claim 1, wherein said CT scanner is a purely-rotational-type CT scanner wherein said scan means rotates the beam of radiation relative to the heart and wherein said control means further comprising means responsive to said pulse signal for generating a gate signal having timing and duration corresponding to the predicted occurrences of said selected phase; and wherein said CT scanner further comprising means responsive to said gate signal for gating the beam on and off synchronously with said selected phase.

10. The apparatus as set forth in claim 9, wherein said means for gating the beam includes controllable shutter means for blocking the beam.

11. A method of producing at least one tomographic image of at least one generally planar slice of a patient's heart in a selectable phase of the cardiac cycle with a CT scanner, the method comprising:

sensing the same functional point in each successive cardiac cycle of the patient and producing a pulse signal indicative of said same functional point;

delaying said pulse signal for a selectable duration for selecting the phase of the cardiac cycle to be imaged;

generating at least one beam of radiation;

scanning said beam relative to the patient's heart;

generating image data indicative of the attenuation of radiation crossing through the planar slice;

monitoring the heart for irregular cardiac cycles including the further steps of:

determining whether the period between successive pulse signals varies from the period of the patient's normal cardiac cycle beyond predetermined limits;

when said period between successive pulse signals varies from the normal cardiac cycle period beyond the predetermined limits, discarding the image data generated during the irregular cardiac cycle;

controlling the processing of image data with said delayed signal to process the image data generated during said same selected phase in successive normal period cardiac cycles; and, constructing a said tomographic image of the planar slice of the heart in said selected phase.

12. The method of cardiac imaging as set forth in claim 11 wherein said scanning step includes:

laterally traversing said beam relative to the heart, commencing said lateral traversing at said same functional point in each successive cardiac cycle whereby the traversing beam reaches the heart at the time of said selected phase in the cardiac cycle; and rotating said beam after each lateral traverse.

13. The method as set forth in claim 11 wherein the scanning step further includes continuously scanning said beam of radiation along a generally circular arc and wherein said image data generating step further includes generating image data generally continuously and wherein said controlling step further includes gating said image data with said delay signal.

* * * * *